United States Patent
Lee et al.

(10) Patent No.: US 8,003,815 B2
(45) Date of Patent: Aug. 23, 2011

(54) METHOD FOR PREPARATION OF CROSS-CONDENSED COMPOUND BETWEEN AMINO ACIDS AND AMINOALKYLSILANE HAVING ALKOXY GROUPS USING MICROWAVE

(75) Inventors: Ik Mo Lee, Incheon (KR); Dong Hwan Lee, Seoul (KR); Ho Sub Kim, Incheon (KR); Sang Eon Park, Incheon (KR)

(73) Assignee: Inha-Industry Partnership Institute, Incheon (KR)

( * ) Notice: Subject to any disclaimer, the term of this patent is extended or adjusted under 35 U.S.C. 154(b) by 0 days.

(21) Appl. No.: 12/739,598

(22) PCT Filed: Feb. 22, 2008

(86) PCT No.: PCT/KR2008/001058
§ 371 (c)(1),
(2), (4) Date: Apr. 23, 2010

(87) PCT Pub. No.: WO2009/054577
PCT Pub. Date: Apr. 30, 2009

(65) Prior Publication Data
US 2010/0249444 A1   Sep. 30, 2010

(30) Foreign Application Priority Data
Oct. 25, 2007 (KR) .................. 10-2007-0107725

(51) Int. Cl.
*C07F 7/04* (2006.01)
(52) U.S. Cl. .................. 556/419; 556/465; 556/466
(58) Field of Classification Search .................. 556/419, 556/465, 466
See application file for complete search history.

(56) References Cited

U.S. PATENT DOCUMENTS

| 5,883,349 A | 3/1999 | Kingston |
| 6,437,167 B1 * | 8/2002 | Sunjic et al. .................. 558/419 |
| 2005/0143592 A1 | 6/2005 | Auner |
| 2007/0232809 A1 | 10/2007 | Kim et al. |

OTHER PUBLICATIONS

Goretzki et al., {Green Polymer Chemistry: Microwave-Assisted Single-Step Synthesis of Various (Meth) Acrylamides and Poly (Meth) Acrylamides Directly from (Meth) Acrylic Acid and Amines, Macromol. Rapid Commun. 2004, vol. 25, pp. 513-516}.*

Goretzki, C. et al., "Green Polymer Chemistry: Microwave-Assisted Single-Step Synthesis of Various (Meth) Acrylamides and Poly (Meth) Acrylamides Directly from (Meth) Acrylic Acid and Amines." Macromol. Rapid Commun. 2004, vol. 25, pp. 513-516, Wiley-VCH Verlag GmbH & Co.

* cited by examiner

*Primary Examiner* — Jafar Parsa
(74) *Attorney, Agent, or Firm* — Greenlee Sullivan PC

(57) ABSTRACT

The present invention provides a method of preparing a cross-condensed compound of an amino-acid derivative and (aminoalkyl)trialkoxysilane using microwave, including: irradiating and heating an amino-acid derivative and (aminoalkyl) trialkoxysilane in a microwave reactor to obtain a reaction product (step 1); and refining the reaction product obtained in the step 1 by removing an unreacted solid material from the reaction product and then leaving the reaction product at room temperature under vacuum to remove excess (aminoalkyl)trialkoxysilane therefrom (step 2). According to the method, since a cross-condensation reaction is performed using microwave, unlike a conventional condensation reaction, economic efficiency is increased due to no catalyst, short reaction time and no solvent. Further, the yield and selectivity of products is increased, and the condensation reaction can be environment-friendly performed because a solvent which can badly influence the environment may not be used.

5 Claims, No Drawings

METHOD FOR PREPARATION OF CROSS-CONDENSED COMPOUND BETWEEN AMINO ACIDS AND AMINOALKYLSILANE HAVING ALKOXY GROUPS USING MICROWAVE

TECHNICAL FIELD

The present invention relates to a method of preparing a cross-condensed compound of an amino acid derivative and aminoalkylsilane having an alkoxy group, and, more particularly, to a method of preparing a cross-condensed compound of an amino acid derivative and aminoalkylsilane having an alkoxy group using microwave, by which high yield and selectivity can be obtained in a short reaction time without using a solvent and a catalyst.

BACKGROUND ART

A condensation reaction is a reaction for forming a new chemical bond between compounds while producing a low molecular weight substance such as water, and is frequently used in organic synthesis. However, generally, the condensation reaction is conducted using a solvent under an acid catalyst, and, according to circumstances, takes much time and requires high-temperature conditions.

In particular, in a condensation reaction in which water is produced, it is very possible to lose a functional group, such as an alkoxysilyl group, to be used in subsequent steps because water is prone to react with the functional group. In order to overcome the above problem, when a protecting group is used, a multistep reaction is adopted to have low yield, a major cause for economic inefficiency.

For example, in order to react (aminoalkyl)trialkoxysilane with dicarboxylic acid, first, dicarboxylic acid is converted into carboxylic acid chloride, and then the carboxylic acid chloride are reacted with (aminoalkyl)trialkoxysilane in the presence of triethylamine. However, such a reaction is problematic in the yield and reaction conditions are not definite [Xiang, S.; Zhang, Y.; Xin, Q.; Li, C. *Angew. Chem. Int. Ed.* 2002, 41(5), 821-824.], and a post-treatment process is very complicated [Katz, A.; Davis, M. E. *Nature,* 2000, 403, 286-289.].

Further, when a substrate, such as amino acid or hydrocarboxylic acid, is used, since the substrate has many functional groups, side reactions may occur due to the self-condensation of the functional groups. Therefore, it is required to introduce a protecting group, and reaction time and production costs are increased due to the increase in the preparative steps.

Accordingly, in recent years, in order to reduce the preparation steps and reaction time and to minimize the formation of volatile organic substances, research on novel synthetic methods which can maintain high yield and selectivity without using a solvent has been variously made.

Considering that environment friendliness and economical utilization of materials have been lately issued, such research on the new synthetic methods is very important. Among the new synthetic methods, a synthetic method using microwaves has lately attracted considerable attention.

A microwave, which is an electromagnetic wave having a frequency of 1~300 GHz and a wavelength of 1 mm~1 m, is called a decimeter wave, a centimeter wave or a millimeter wave.

One of the household electric appliances using a microwave is a microwave oven. The microwave oven increases the temperature of foods by applying an electromagnetic wave having a small length of 1~2 mm to water present in the foods, thus causing water particles to collide with each other.

Such a microwave having various uses began to be applied to organic reactions in the mid-1980s. Thereafter, it was reported in several thousand theses that reaction rate was remarkably increased using the microwave [Lidstrom, P.; Tierney, J.; Wathey, B.; Westman, J. *Tetrahedron* 2001, 57, 9225-9283.; Lathed, M.; Hallberg, A. *Drug Discovery Today* 2001, 6, 406-416.].

The synthetic method using the microwave has well known advantages in that high yield can be obtained with little side products, reactants and solvents having low toxicity and reactivity are used, and experimental methods are simple. Thus, this method is chiefly used in environment-friendly organic reactions [Larhed, M.; Moberg, C.; Hallberg, A. *Acc. Chem. Res.* 2002, 35, 717-727.].

However, a conventional microwave reactor was problematic in that the wavelength of the microwave emitted therefrom was not constant, hot spots occurred, and safeness was not ensured, thereby decreasing reproducibility, but a recently developed microwave reactor overcame such problems to improve the reproducibility.

In many catalytic reactions, a catalytic reaction using a heterogeneous catalyst is advantageous in that a process for separating products may not be conducted for a long time and the recovery of the catalyst is easy, compared to a homogeneous catalytic reaction. Owing to these advantages of the heterogeneous catalyst, recently, many efforts to develop catalytic systems for asymmetric synthesis have been made.

As one of the efforts, in the case of asymmetric epoxidation, a polymer-supported catalytic system was developed using tartarate ester introduced into a polystyrene resin, but its chiral induction effect (about 50~60%) was limited [Farrall, M. J.; Alexis, M.; Trecarten, M. *Nouv. J. Chim.* 1983, 7, 449.].

Further, when a polymer-supported catalytic system was developed using tartarate ester introduced into an inorganic material, the developed catalytic system had a problem of reproducibility [Choudary, B. M.; Valli, V. L. K.; Prasad, A. D. *J. Chem. Soc. Chem. Commun.* 1990, 1186. Baiker, A], and, when a polymer-supported catalytic system was developed using a gel-type polymeric ligand, the developed catalyst system had a problem of swelling during a reaction [Karjalainen, J. K.; Hormi, O. E. O.; Sherrington, D. C. *Tetrahedron: Asymmetry* 1998, 9, 2019.].

In order to solve the above problems, interest in the use of organic-inorganic hybrid materials has increased [Moreau, J. J. E.; Vellutini, L.; Man, M. W. C.; Bied, C. *J. Am. Chem. Soc.* 2001, 123, 1509-1510; Defreese, J. L.; Katz, A. *Chem. Mater.* 2005, 17, 6503-6506.].

Unlike organic polymers, the organic-inorganic hybrid materials do not swell or dissolve in organic solvents, and exhibit excellent mechanical and thermal stability.

Further, in the organic-inorganic hybrid materials, since their organic moieties are covalently bonded with inorganic materials, the possibility of leaching is decreased, and thus it is expected that the use of organic-inorganic hybrid materials will be expanded in the future.

Among these organic-inorganic hybrid materials, chiral catalytic materials having enantioselectivity particularly become the focus of attention, and it is very important to design and synthesize catalysts using chiral catalytic materials.

Considering the characteristics of the organic-inorganic hybrid materials and the chiral catalytic materials, in the present invention, it is determined that they can be easily changed such that they have functional groups serving to introduce amino acid, which can be coordinatively bonded with metals to have high enantiomeric purity, economic efficiency and catalytic activity, into inorganic materials.

Therefore, the present inventors have made efforts to overcome the disadvantages of the conventional synthetic methods, in that solvent and catalyst must be used, long reaction time is required, high-temperature conditions are required, and protecting groups must be used. As a result, we found a method of preparing a compound, in which an amino-acid derivative and aminoalkylsilane having an alkoxy group are condensed, using microwaves without solvent and catalyst for a short reaction time, high selectivity and high yield while maintaining the high reactivity of functional group. Based on these findings, the present invention was completed.

DISCLOSURE

Technical Problem

Accordingly, an object of the present invention is to provide a method of preparing a cross-condensed compound of amino acid and (aminoalkyl)trialkoxysilane using microwave without solvent and catalyst at a high selectivity and high yield, by which organic compounds having amino groups and alkoxysilyl groups, which are terminal groups having various uses, can be environment-friendly prepared.

Technical Solution

In order to accomplish the above object, the present invention provides a method of preparing a cross-condensed compound of amino acid and aminoalkylsilane having an alkoxy group using microwave.

Advantageous Effects

According to the present invention, since a cross-condensation reaction is performed using microwave, unlike a conventional condensation reaction, economic efficiency is increased due to no catalyst, short reaction time and no solvent. Further, the yield and selectivity of products are increased, and the condensation reaction can be environment-friendly performed because a solvent which can badly influence the environment may not be used.

BEST MODE

The present invention provides a method of preparing a cross-condensed compound of an amino-acid derivative and (aminoalkyl)trialkoxysilane using microwave, including: irradiating and heating an amino-acid derivative and (aminoalkyl)trialkoxysilane in a microwave reactor to obtain a reaction product, as represented by the following Reaction Formula 1 (step 1); and refining the reaction product obtained in the step 1 by removing an unreacted solid material from the reaction product and then leaving the reaction product at room temperature under vacuum to remove excess (aminoalkyl)trialkoxysilane therefrom (step 2).

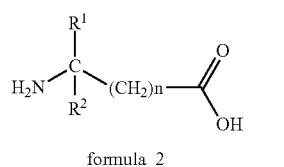

formula 2

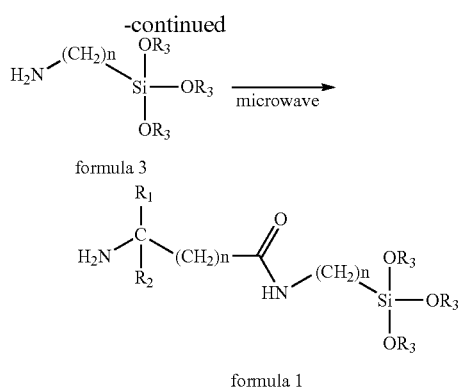

formula 3 formula 1 wherein $R^1$, $R^2$ and $R^3$ are each independently or selectively a straight-chain or branched chain alkyl group of $C_1$~$C_8$, or an aryl group of $C_5$~$C_{10}$, which is unsubstituted or substituted with halogen atoms; wherein $R^1$ and $R^2$ can each independently or selectively be H, and wherein m is an integer of 1 to 8 and n is an integer from 0 to 7.

Hereinafter, the method according to the present invention is described in more detail by steps.

In step 1, an amino-acid derivative 2 and (aminoalkyl)trialkoxysilane 3 are irradiated and heated in a microwave reactor to obtain a reaction product.

It is preferred that the power of the microwave reactor be 60~300 W. When the power of the microwave reactor is less than 60 W, reactants cannot be rapidly heated to a reaction temperature and a reaction time is increased, so that side products, such as dimers, trimers and the like, are formed, with the result that the yield of the compound is relatively decreased. In contrast, when the power thereof is more than 300 W, reactants or products can be decomposed, and reaction occurs instantaneously and thus the instantaneous temperature of the microwave reactor reaches 200° C. or more, so that (aminoalkyl)trialkoxysilane is instantaneously vaporized, with the result that there is a danger that the microwave reactor is exploded.

Further, it is preferred that the reaction temperature of the microwave reactor be 60~200° C. When the reaction temperature of the microwave reactor is less than 60° C., reaction does not proceed. In contrast, when the reaction temperature thereof is more than 200° C., side products, such as dimers, trimers and the like, are formed and thus the yield of product is greatly decreased, and the side products are highly volatile materials and thus there is a danger that the microwave reactor is exploded.

In step 2, an unreacted solid material is removed from the reaction product obtained in step 1, and then the reaction product is left at room temperature under vacuum to remove excess (aminoalkyl)trialkoxysilane therefrom, thereby refining the reaction product.

In this step, when the condensation reaction of amino acid and (aminoalkyl)trialkoxysilane is conducted using microwave, since the reaction product obtained in step 1 includes a small amount of unreacted solid amino acid, the unreacted solid amino acid is removed, and then the reaction product is left at room temperature under vacuum to remove unreacted liquid (aminoalkyl)trialkoxysilane therefrom, thereby increasing the purity of the reaction product.

In this case, it is preferred that the reaction product be left for 1~3 hours. When the reaction product is left for less than 1 hour, reactants can remain. In contrast, when the reaction product is left for more than 3 hours, even products can be removed, and thus the yield of the products can be decreased. Further, when the reaction product is refined at a temperature lower than room temperature, the excess unreacted liquid (aminoalkyl)trialkoxysilane cannot be easily removed, and, when the reaction product is again heated to room temperature, side products, such as dimers, trimers and the like, can be formed.

MODE FOR INVENTION

Hereinafter, the present invention will be described in detail with reference to the following Examples. Here, the following Examples are set forth to illustrate the present invention, but the scope and spirit of the present invention are not limited thereto.

Example 1

Preparation of a Cross-Condensed Compound of Phenylalanine and (3-Aminopropyl)Triethoxysilane Step 1: Preparation of a Cross-Condensed Compound of Phenylalanine and (3-Aminopropyl)Triethoxysilane 0.7 g (4.2 mmol) of phenylalanine and 1.5 ml (5.8 mmol) of (3-aminopropyl)triethoxysilane were put into a microwave reactor (CEM Co. Discover), heated to a temperature of 160° C. using a power of 300 W, and then maintained for 3 minutes to obtain a target compound (1.65 g, 105%).

Step 2: Refinement of a Cross-Condensed Compound of Phenylalanine and (3-Aminopropyl)Triethoxysilane The target compound obtained in step 1 was rapidly filtered, and thus unreacted solid materials were removed therefrom. Subsequently, the filtered target compound was left for 12 hours at room temperature under vacuum, and thus unreacted excess (3-aminopropyl)triethoxysilane was removed therefrom. Thereafter, whether or not impurities were present in the resulting target compound was observed using NMR (Nuclear Magnetic Resonance) spectroscopy. As a result, when impurities were present in the resulting target compound, the resulting target compound was dissolved in an organic solvent such as diethyl ether or methylene chloride and then filtered using celite, and then the organic solvent was removed therefrom at room temperature under vacuum to obtain a refined target compound (1.47 g, 95%).

$^1$H NMR (400 MHz, CDCl$_3$): 7.5 (br, 1H NH), 7.32-7.19 (m, 5H, Ph), 3.87-3.75 (m, 6H, OCH$_2$CH$_3$), 3.51 (br, 1H, CH$_2$CHNH$_2$), 3.27-3.22 (m, 2H, PhCH$_2$, NHCH$_2$), 2.68-2.63 (m, 2H, PhCH$_2$), 1.61-1.51 (br, 2H, H$_2$NCH), 1.41-1.34 (m, 2H, CH$_2$CH$_2$CH$_2$), 1.28-1.19 (m, 9H, OCH$_2$CH$_3$), 0.67-0.57 (m, 2H, SiCH$_2$)

$^{13}$C NMR (100 MHz, CDCl$_3$): 174.1 (C=O), 138.0, 129.2, 128.5, 126.7 (Ph), 58.4 (OCH$_2$), 56.6 (OCH$_2$CH$_3$), 45.1 (CHNH$_2$), 41.6 (NHCH$_2$), 41.2 (PhCH$_2$), 27.3 (CH$_2$CH$_2$CH$_2$), 18.4 (OCH$_2$CH$_3$), 8.2 (CH$_2$Si)

LC/MS (THF): m/z=391.2034, [M+Na-1]+; 538.2745, [Ph-Si (OH)$_2$—O—Si (OH)$_2$-Ph-2H$_2$O+Na]+

MS (DIP-MS): m/z=368 (12) (M+), 326(10), 284(15), 250 (35), 208(50), 192(20), 160 (6)

Anal. Calcd. for C$_{18}$H$_{32}$O$_4$N$_2$Si: C, 58.66; H, 8.75; N, 7.60. Found: C, 58.89; H, 8.20; N, 7.62.

Example 2

Preparation of a Cross-Condensed Compound of Valine and (3-Aminopropyl)Triethoxysilane Step 1: Preparation of a Cross-Condensed Compound of Valine and (3-Aminopropyl)Triethoxysilane 0.53 g (4.5 mmol) of valine and 1.5 ml (5.8 mmol) of (3-aminopropyl)triethoxysilane were put into a microwave reactor, heated to a temperature of 170° C. using a power of 300 W, and then maintained for 3 minutes to obtain a target compound (1.51 g, 105%).

Step 2: Refinement of a Cross-Condensed Compound of Valine and (3-Aminopropyl)Triethoxysilane The target compound obtained in step 1 was rapidly filtered, and thus unreacted solid materials were removed therefrom. Subsequently, the filtered target compound was left for 12 hours at room temperature under vacuum, and thus unreacted excess (3-aminopropyl)triethoxysilane was removed therefrom. Thereafter, whether or not impurities were present in the resulting target compound was observed using NMR (Nuclear Magnetic Resonance). As a result, when impurities were present in the resulting target compound, the resulting target compound was dissolved in an organic solvent such as diethyl ether or methylene chloride and then filtered using celite, and then the organic solvent was removed therefrom at room temperature under vacuum to obtain a refined target compound (1.36 g, 90%).

$^1$H NMR (400 MHz, CDCl$_3$): 7.45 (br, 1H NH), 3.85-3.79 (m, 6H$_2$OCH$_2$CH$_3$), 3.42-3.2 (m, 2H, CH$_2$CHNH$_2$), 2.68-2.63 (m, 2H, NHCH$_2$), 2.30 (br, 1H, CH$_3$CH), 1.65-1.48 (m, 3H, H$_2$NCH, CH$_2$CH$_2$CH$_2$), 1.25-1.19 (m, 9H, OCH$_2$CH$_3$), 0.98 (d, 3H, J=7.2, CH$_3$CH), 0.84 (d, 3H, J=7.2, CH$_3$CH), 0.65-0.61 (m, 2H, SiCH$_2$)

$^{13}$C NMR (100 MHz, CDCl$_3$): 173.8 (C=O), 60.0 (CHNH$_2$), 58.0 (OCH$_2$CH$_3$), 44.8 (CH$_2$NH), 30.7 (CHCH$_3$), 27.0 (CH$_2$CH$_2$CH$_2$), 19.5, 15.6 (CH(CH$_3$)$_2$), 18.1 (OCH$_2$CH$_3$), 7.6 (CH2Si)

LC/MS (THF): m/z=343.2025, [M+Na-1]+; 589.3420, [Val-Si(OEt)$_2$-O—Si (OEt)-2-Val+Na]+

MS (DIP-MS) m/z 320 (25) (M+), 278(15), 263(40), 236 (36), 22 (12?), 208 (34), 194 (58), 144 (52).

Example 3

Preparation of a Cross-Condensed Compound of Alanine and (3-Aminopropyl)Triethoxysilane Step 1: Preparation of a Cross-Condensed Compound of Alanine and (3-Aminopropyl)Triethoxysilane 0.4 g (4.5 mmol) of alanine and 1.5 ml (5.8 mmol) of (3-aminopropyl)triethoxysilane were put into a microwave reactor, heated to a temperature of 200° C. using a power of 300 W, and then maintained for 3 minutes to obtain a target compound (1.32 g, 100%).

Step 2: Refinement of a Cross-Condensed Compound of Alanine and (3-Aminopropyl)Triethoxysilane The target compound obtained in step 1 was rapidly filtered, and thus unreacted solid materials were removed therefrom. Subsequently, the filtered target compound was left for 12 hours at room temperature under vacuum, and thus unreacted excess (3-aminopropyl)triethoxysilane was removed therefrom. Thereafter, whether or not impurities were present in the resulting target compound was observed using NMR (Nuclear Magnetic Resonance). As a result, when impurities were present in the resulting target compound, the resulting target compound was dissolved in an organic solvent such as diethyl ether or methylene chloride and then filtered using celite, and then the organic solvent was removed therefrom at room temperature under vacuum to obtain a refined target compound (1.12 g, 85%).

$^1$H NMR (400 MHz, CDCl$_3$): 7.5 (br, 1H NH), 3.85-3.79 (m, 6H$_2$OCH$_2$CH$_3$), 3.5 (m, 1H, CH$_2$CHNH$_2$), 3.23 (m, 1H, CH$_2$CHNH$_2$), 2.68-2.66 (m, 2H, NHCH$_2$), 2.30 (br, 1H, CH$_3$CH), 1.7-1.45 (m, 3H, H$_2$NCH, CH$_2$CH$_2$CH$_2$), 1.31 (m, 3H, CHCH$_3$), 1.25-1.19 (m, 9H, OCH$_2$CH$_3$), 0.98 (d, 3H, J=7.2, CH$_3$CH), 0.84 (d, 3H, J=7.2, CH$_3$CH), 0.65-0.61 (m, 2H, SiCH$_2$)

$^{13}$C NMR (100 MHz, CDCl$_3$): 175.5 (C=O), 60.0 (CHNH$_2$), 58.4 (OCH$_2$CH$_3$), 50.92 (CHCH$_3$), 45.2 (CH$_2$NH), 27.4 (CH$_2$CH$_2$CH$_2$), 22.0 (CHCH$_3$), 18.4 (OCH$_2$CH$_3$), 7.9 (CH$_2$Si)

LC/MS (THF): m/z=315.1734, [M+Na-1]+; 533.2818, [Ala-Si(OEt)$_2$-O—Si(OEt)$_2$-Ala+Na]+

MS (DIP-MS) m/z 292 (15) (M+), 250(28), 208(45), 193 (30), 116 (80).

Example 4

Preparation of a Cross-Condensed Compound of Leucine and (3-Aminopropyl)Triethoxysilane Step 1: Preparation of a Cross-Condensed Compound of Leucine and (3-Aminopropyl)Triethoxysilane 0.58 g (4.5 mmol) of leucine and 1.5 ml (5.8 mmol) of (3-aminopropyl)triethoxysilane were put into a microwave reactor, heated to a temperature of 200° C. using a power of 300 W, and then maintained for 3 minutes to obtain a target compound (1.48 g, 99%).

Step 2: Refinement of a Cross-Condensed Compound of Leucine and (3-Aminopropyl)Triethoxysilane The target compound obtained in step 1 was rapidly filtered, and thus unreacted solid materials were removed therefrom. Subsequently, the filtered target compound was left for 12 hours at room temperature under vacuum, and thus unreacted excess (3-aminopropyl)triethoxysilane was removed therefrom. Thereafter, whether or not impurities were present in the resulting target compound was observed using NMR (Nuclear Magnetic Resonance). As a result, when impurities were present in the resulting target compound, the resulting target compound was dissolved in an organic solvent such as diethyl ether or methylene chloride and then filtered using celite, and then the organic solvent was removed therefrom at room temperature under vacuum to obtain a refined target compound (1.28 g, 85%).

$^1$H NMR (400 MHz, CDCl$_3$): 7.4 (br, 1H NH), 3.85-3.79 (m, 6H$_2$OCH$_2$CH$_3$), 3.35 (m, 1H, CH$_2$CHNH$_2$), 3.23 (m, 1H, CH$_2$CHNH$_2$), 2.70-2.65 (m, 2H, NHCH$_2$), 1.7-1.45 (m, 5H, CH$_3$CHCH$_2$, CH$_2$CH$_2$CH$_2$), 1.25-1.18 (m, 9H, OCH$_2$CH$_3$), 0.97 (m, 6H, CH$_3$CH), 0.66-0.61 (m, 2H, SiCH$_2$)

$^{13}$C NMR (100 MHz, CDCl$_3$): 175.1 (C=O), 58.1 (OCH$_2$CH$_3$), 53.4 (CHNH$_2$), 44.9 (CH$_2$CHNH$_2$), 44.1 (CH$_2$NH), 27.1 (CH$_2$CH$_2$CH$_2$), 24.7, 23.3 (CHCH$_3$), 21.2 (CHCH$_3$), 18.1 (OCH$_2$CH$_3$), 7.4 (CH$_2$Si)

MS (DIP-MS) m/z 334 (18) (M+), 306(10), 292(20), 262 (40), 250 (50), 208 (45), 179 (100).

Example 5

Preparation of a Cross-Condensed Compound of Glycine and (3-Aminopropyl)Triethoxysilane Step 1: Preparation of a Cross-Condensed Compound of Glycine and (3-Aminopropyl)Triethoxysilane 0.35 g (4.6 mmol) of glycine and 1.5 ml (5.8 mmol) of (3-aminopropyl)triethoxysilane were put into a microwave reactor, heated to a temperature of 200° C. using a power of 300 W, and then maintained for 3 minutes to obtain a target compound (1.29 g, 101%).

Step 2: Refinement of a Cross-Condensed Compound of Glycine and (3-Aminopropyl)Triethoxysilane The target compound obtained in step 1 was rapidly filtered, and thus unreacted solid materials were removed therefrom. Subsequently, the filtered target compound was left for 12 hours at room temperature under vacuum, and thus unreacted excess (3-aminopropyl)triethoxysilane was removed therefrom. Thereafter, whether or not impurities were present in the resulting target compound was observed using NMR (Nuclear Magnetic Resonance). As a result, when impurities were present in the resulting target compound, the resulting target compound was dissolved in an organic solvent such as diethyl ether or methylene chloride and then filtered using celite, and then the organic solvent was removed therefrom at room temperature under vacuum to obtain a refined target compound (1.16 g, 90%).

$^1$H NMR (400 MHz, CDCl$_3$): 7.6 (br, 1H NH), 3.83-3.70 (m, 6H, OCH$_2$CH$_3$), 3.3-3.26 (m, 2H, CH$_2$NH$_2$) 3.23 (m, 1H, CH$_2$CHNH$_2$), 2.70-2.66 (m, 2H, NHCH$_2$), 1.66-1.51 (m, 4H, H$_2$NCH, CH$_2$CH$_2$CH$_2$), 1.28-1.21 (m, 9H, OCH$_2$CH$_3$), 0.67-0.61 (m, 2H, SiCH$_2$)

$^{13}$C NMR (100 MHz, CDCl$_3$): 172.3 (C=O), 58.2 (OCH$_2$CH$_3$), 50.92 (CHCH$_3$), 45.0 (CH$_2$NH$_2$), 44.7 (CH$_2$NH), 27.2 (CH$_2$CH$_2$CH$_2$), 18.2 (OCH$_2$CH$_3$), 7.6 (CH$_2$Si)

MS (DIP-MS) m/e 278 (50) (M+), 262(20), 249 (15) 236 (20), 207 (15), 165 (45).

Example 6

Preparation of a Cross-Condensed Compound of Proline and (3-Aminopropyl)Triethoxysilane Step 1: Preparation of a Cross-Condensed Compound of Proline and (3-Aminopropyl)Triethoxysilane 0.58 g (5.0 mmol) of proline and 1.5 ml (5.8 mmol) of (3-aminopropyl)triethoxysilane were put into a microwave reactor, heated to a temperature of 200° C. using a power of 300 W, and then maintained for 3 minutes to obtain a target compound (1.64 g, 103%).

Step 2: Refinement of a Cross-Condensed Compound of Proline and (3-Aminopropyl)Triethoxysilane The target compound obtained in step 1 was rapidly filtered, and thus unreacted solid materials were removed therefrom. Subsequently, the filtered target compound was left for 12 hours at room temperature under vacuum, and thus unreacted excess (3-aminopropyl)triethoxysilane was removed therefrom. Thereafter, whether or not impurities were present in the resulting target compound was observed using NMR (Nuclear Magnetic Resonance). As a result, when impurities were present in the resulting target compound, the resulting target compound was dissolved in an organic solvent such as diethyl ether or methylene chloride and then filtered using celite, and then the organic solvent was removed therefrom at room temperature under vacuum to obtain a refined target compound (1.16 g, 90%).

$^1$H NMR (400 MHz, CDCl$_3$): 7.7 (br, 1H NH), 3.85-3.71 (m, 6H$_2$OCH$_2$CH$_3$), 3.69 (m, 1H, CHNH), 3.23 (m, 2H, CH$_2$CHNH$_2$), 3.0-2.8 (m, 2H, NHCH$_2$CH$_2$CH$_2$CH) 2.70-2.66 (m, 2H, NHCH$_2$), 2.11, 1.82 (m, 2H, NHCH$_2$CH$_2$CH$_2$CH), 1.75-1.31 (m, 5H, NHCH$_2$CH$_2$CH$_2$CH, CH$_2$CH$_2$CH$_2$), 1.25-1.19 (m, 9H, OCH$_2$CH$_3$) 0.65-0.61 (m, 2H, SiCH$_2$)

$^{13}$C NMR (100 MHz, CDCl$_3$): 174.7 (C=O), 60.48 (CHNH), 58.2 (OCH$_2$CH$_3$), 47.11, 30.7, 27.1 (NHCH$_2$CH$_2$CH$_2$CH) 44.5 (CH$_2$NH), 27.0 (CH$_2$CH$_2$CH$_2$), 18.2 (OCH$_2$CH$_3$), 7.4 (CH$_2$Si)

MS (DIP-MS) m/e 318 (12) (M+), 304(10), 276(15), 263 (10), 234(25), 193(40), 162(100), 135 (80)

Anal. Calcd. for C$_{14}$H$_{18}$O$_4$N$_2$Si: C, 52.80; H, 9.49; N, 8.80. Found: C, 52.43; H, 9.03; N, 8.42.

Example 7

Preparation of a Cross-Condensed Compound of Cysteine and (3-Aminopropyl)Triethoxysilane

Step 1: Preparation of a Cross-Condensed Compound of Cysteine and (3-Aminopropyl)Triethoxysilane 0.6 g (5.0 mmol) of cysteine and 1.5 ml (5.8 mmol) of (3-aminopropyl)triethoxysilane were put into a microwave reactor, heated to a temperature of 200° C. using a power of 300 W, and then maintained for 3 minutes to obtain a target compound (1.72 g, 104%).

Step 2: Refinement of a Cross-Condensed Compound of Cysteine and (3-Aminopropyl)Triethoxysilane The target compound obtained in step 1 was rapidly filtered, and thus unreacted solid materials were removed therefrom. Subsequently, the filtered target compound was left for 12 hours at room temperature under vacuum, and thus unreacted excess (3-aminopropyl)triethoxysilane was removed therefrom. Thereafter, whether or not impurities were present in the resulting target compound was observed using NMR (Nuclear Magnetic Resonance). As a result, when impurities were present in the resulting target compound, the resulting target compound was dissolved in an organic solvent such as diethyl ether or methylene chloride and then filtered using celite, and then the organic solvent was removed therefrom at room temperature under vacuum to obtain a refined target compound (1.46 g, 90%).

$^1$H NMR (400 MHz, CDCl$_3$): 7.6 (br, 1H NH), 3.87-3.76 (m, 6H, OCH$_2$CH$_3$), 3.50 (br, 1H, CHNH$_2$) 3.25 (br, 1H, CHNH$_2$), 3.01, 2.81 (m, 2H, CH$_2$SH), 2.70-2.66 (m, 2H, NHCH$_2$), 1.61-1.51 (m, 2H, NHCH$_2$CH$_2$CH$_2$CH) 1.41 (s, 2H, CHSH, CHNH$_2$), 1.24-1.18 (m, 9H, OCH$_2$ CH$_3$), 0.66-0.60 (m, 2H, SiCH$_2$)

$^{13}$C NMR (100 MHz, CDCl$_3$): 172.0 (C=O), 58.17 (OCH$_2$CH$_3$), 56.08 (CHNH$_2$), 44.9 (CH$_2$NH), 30.40 (CH$_2$SH) 27.08 (CH$_2$CH$_2$CH$_2$), 18.2 (OCH$_2$CH$_3$), 7.4 (CH$_2$Si)

MS (DIP-MS) m/z 324 (35) (M+), 308(15), 292(20), 282 (15), 276(25), 261(13), 219(54), 177(100), 137 (50)

Anal. Calcd. for C$_{12}$H$_{28}$O$_4$N$_2$Si: C, 44.41; H, 8.70; N, 8.63. S, 9.88. Found: C, 44.43; H, 9.13; N, 8.38; S, 9.71.

Example 8

Preparation of a Cross-Condensed Compound of Lysine and (3-Aminopropyl)Triethoxysilane

Step 1: Preparation of a Cross-Condensed Compound of Lysine and (3-Aminopropyl)Triethoxysilane 0.65 g (4.5 mmol) of lysine and 1.5 ml (5.8 mmol) of (3-aminopropyl)triethoxysilane were put into a microwave reactor, heated to a temperature of 200° C. using a power of 300 W, and then maintained for 3 minutes to obtain a target compound (1.70 g, 110%).

Step 2: Refinement of a Cross-Condensed Compound of Lysine and (3-Aminopropyl)Triethoxysilane The target compound obtained in step 1 was rapidly filtered, and thus unreacted solid materials were removed therefrom. Subsequently, the filtered target compound was left for 12 hours at room temperature under vacuum, and thus unreacted excess (3-aminopropyl)triethoxysilane was removed therefrom. Thereafter, whether or not impurities were present in the resulting target compound was observed using NMR (Nuclear Magnetic Resonance). As a result, when impurities were present in the resulting target compound, the resulting target compound was dissolved in an organic solvent such as diethyl ether or methylene chloride and then filtered using celite, and then the organic solvent was removed therefrom at room temperature under vacuum to obtain a refined target compound (1.34 g, 85%).

$^1$H NMR (400 MHz, CDCl$_3$): 7.5 (br, 1H NH), 3.85-3.79 (m, 6H$_2$OCH$_2$CH$_3$), 3.40-3.18 (m, 3H, CHNH$_2$, NHCH$_2$), 2.70-2.66 (m, 4H, CH$_2$NH$_2$, NH$_2$CH$_2$CH$_2$CH$_2$CH$_2$CH$_2$CH) 1.82 (m, 2H, CH$_2$NH$_2$), 1.71-1.41 (m, 8H, NH$_2$CH$_2$CH$_2$CH$_2$CH$_2$CH), 1.24-1.20 (m, 9H, OCH$_2$CH$_3$), 0.65-0.61 (m, 2H, SiCH$_2$)

$^{13}$C NMR (100 MHz, CDCl$_3$): 174.0 (C=O), 57.93 (OCH$_2$CH$_3$), 54.9 (CHNH$_2$), 53.55 (CH$_2$NH), 30.40 (CH$_2$SH) 27.08 (CH$_2$CH$_2$CH$_2$), 17.98 (OCH$_2$CH$_3$), 7.23 (CH$_2$Si)

MS (DIP-MS) m/z 349 (25) (M+), 307(40), 292(15), 265 (20), 250 (10), 221 (15), 207 (50), 179 (80).

The invention claimed is:
1. A method of preparing a cross-condensed compound of an amino acid derivative and (aminoalkyl)trialkoxysilane using microwaves, wherein said amino acid derivative has the formula 2:

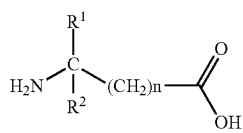

and wherein the (aminoalkyl)trialkoxysilane has the formula 3:

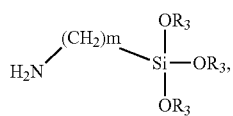

and the cross-condensed compound of an amino acid derivative and (aminoalkyl)trialkoxysilane has the formula 1:

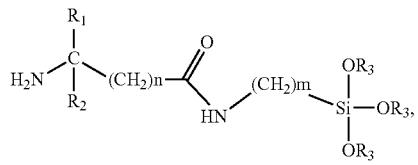

wherein said method comprises the steps of:
1) irradiating and heating an amino-acid derivative of formula 2 and (aminoalkyl)trialkoxysilane of formula 3 in a microwave reactor to obtain a reaction product of formula 1; and
2) refining the reaction product obtained in the step a) by removing an unreacted solid material from the reaction product and then leaving the reaction product at room temperature under vacuum to remove excess,
wherein $R_1$ and $R_2$ are each independently or selectively H, a straight-chain or a branched-chain alkyl group of $C_1$-$C_7$, or an aryl group of $C_5$-$C_{10}$ which is unsubstituted or substituted with halogen atoms, and $R_3$ is independently or selectively a straight-chain or a branched-chain alkyl group of $C_1$-$C_8$, or an aryl group of $C_5$-$C_{10}$, which is unsubstituted or substituted with halogen atoms, wherein n is an integer of 0 to 7; and wherein m is an integer of 1 to 8.

2. The method according to claim 1, wherein the microwave reactor has a power of 60~300 W.

3. The method according to claim 1, wherein the microwave reactor has a reaction temperature of 60~200° C.

4. The method according to claim 1, wherein, in the step 2, the reaction product is left for 1~3 hours.

5. The method according to claim 1, wherein, the reaction in the step 1 is performed without using a solvent and a catalyst.

* * * * *